(12) United States Patent
Knappe et al.

(10) Patent No.: US 9,421,158 B2
(45) Date of Patent: Aug. 23, 2016

(54) AGENT AND METHOD FOR THE TEMPORARY DEFORMATION OF KERATIN FIBRES

(71) Applicant: Henkel AG & Co. KGaA, Duesseldorf (DE)

(72) Inventors: Thorsten Knappe, Schenefeld (DE); Marcus Noll, Norderstedt (DE)

(73) Assignee: Henkel AG & Co. KGaA, Dusseldorf (DE)

(*) Notice: Subject to any disclaimer, the term of this patent is extended or adjusted under 35 U.S.C. 154(b) by 0 days.

(21) Appl. No.: 14/620,265

(22) Filed: Feb. 12, 2015

(65) Prior Publication Data

US 2015/0150777 A1    Jun. 4, 2015

Related U.S. Application Data

(63) Continuation of application No. PCT/EP2013/064580, filed on Jul. 10, 2013.

(30) Foreign Application Priority Data

Aug. 13, 2012  (DE) .................. 10 2012 214 380

(51) Int. Cl.

| *A61K 8/72* | (2006.01) |
|---|---|
| *A61K 8/73* | (2006.01) |
| *A61K 8/81* | (2006.01) |
| *A61Q 5/06* | (2006.01) |
| *A61K 8/92* | (2006.01) |
| *A61Q 19/00* | (2006.01) |

(52) U.S. Cl.
CPC ............ *A61K 8/8147* (2013.01); *A61K 8/732* (2013.01); *A61K 8/8152* (2013.01); *A61K 8/8176* (2013.01); *A61K 8/922* (2013.01); *A61K 8/927* (2013.01); *A61Q 5/06* (2013.01); *A61Q 19/00* (2013.01)

(58) Field of Classification Search
None
See application file for complete search history.

(56) References Cited

U.S. PATENT DOCUMENTS

| 7,056,346 B1 * | 6/2006 | Maubru ................ A61Q 5/065 534/683 |
|---|---|---|
| 8,790,628 B2 | 7/2014 | Schweinsberg et al. |
| 2004/0241105 A1 * | 12/2004 | Riedel .................... A61K 8/046 424/47 |
| 2006/0051311 A1 | 3/2006 | Walter et al. |
| 2013/0108572 A1 | 5/2013 | Balcke et al. |

FOREIGN PATENT DOCUMENTS

DE    102010063842 A1    6/2012

OTHER PUBLICATIONS

PCT International Search Report (PCT/EP2013/064580) dated Jul. 16, 2014.
Database GNPD [Online] Mintel, "FishGlue Matt Styling Gel", XP002727218, Database accession No. 1504937, Nov. 2010.

* cited by examiner

*Primary Examiner* — Susan Tran
(74) *Attorney, Agent, or Firm* — P. Scott Smith

(57) ABSTRACT

Cosmetic preparations based on hydrophobically modified (meth)acrylic acid copolymers and hydrophobically modified polysaccharides are described, together with related methods of use thereof for the temporary shaping of keratin-containing fibers, in particular human hair.

15 Claims, No Drawings

AGENT AND METHOD FOR THE TEMPORARY DEFORMATION OF KERATIN FIBRES

FIELD OF THE INVENTION

The present invention generally relates to the use of cosmetic agents for the temporary shaping of keratinic fibers, in particular human hair. The invention also provides specific agents for the temporary shaping of keratinic fibers.

BACKGROUND OF THE INVENTION

Styling agents for the shaping of keratin-containing fibers have long been known and are used in various embodiments to construct, refresh and set hairstyles which for many hair types can only be achieved by the use of active fixing agents. Both hair treatment agents serving to permanently shape the hair and those used for its temporary shaping have an important role to play here.

Agents for temporary shaping are available in various presentation forms, wherein among the propellant-free agents hair waxes and hair gels in particular are widespread. From a consumer perspective these agents differ from one another in particular also in terms of the product feel. The feel of a hair cosmetic is generally not the chance result of a combination of specific active agents; rather, along with other sensory properties such as appearance and odor, it is an essential means of supporting the product or brand proposition and is thus an important factor in the commercial success of the product.

The problem of the present patent application was therefore to provide cosmetic agents for the temporary shaping of keratinic fibers, having a novel feel and good cosmetic properties. In particular, the feel of the cosmetic agents should differ from the gels and waxes hitherto available on the market.

It was determined that these problems can be solved by a combination of hydrophobically modified (meth)acrylic acid copolymers and hydrophobically modified polysaccharides. Hair cosmetics agents based on this combination of active agents are characterized not only by a unique feel but also by good fixing properties, for example a high degree of hold combined with low stickiness, high flexibility and good moisture resistance—in particular resistance to perspiration and water. The combination of hydrophobically modified (meth)acrylic acid copolymers and hydrophobically modified polysaccharides is also suitable for producing compositions having a stable viscosity.

Cosmetic or dermatological light stabilizing preparations, which in addition to further ingredients contain an acrylates/C10-30 alkyl acrylate crosspolymer and an aluminum starch octenylsuccinate, are described in the German laid-open patent application DE 10 2010 063 842 A1 (Beiersdorf).

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Use of a cosmetic composition, containing at least one hydrophobically modified (meth)acrylic acid copolymer and at least one hydrophobically modified polysaccharide for the temporary shaping of keratin-containing fibers, in particular human hair.

A cosmetic composition, containing at least one hydrophobically modified (meth)acrylic acid copolymer, at least one hydrophobically modified polysaccharide, and at least one wax.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present application firstly provides the use of a cosmetic composition, containing
a) at least one hydrophobically modified (meth)acrylic acid copolymer;
b) at least one hydrophobically modified polysaccharide;
for the temporary shaping of keratin-containing fibers, in particular human hair.

The agents used according to the invention are characterized by a rubber-like consistency. This consistency makes the agents easy to dispense and apply.

The use according to the invention is preferably achieved in that the keratinic fibers are treated with one of the cosmetic compositions described above and temporarily fixed in their shape. The treatment of the keratinic fibers with the cosmetic composition preferably takes place by applying the cosmetic composition to the fingers or to the palms of the hand and then shaping the keratinic fibers with the fingers or palms, as a result of which at least some of the cosmetic composition is transferred from the fingers or the palms to the keratinic fibers.

The use of a cosmetic composition containing
a) at least one hydrophobically modified (meth)acrylic acid copolymer;
b) at least one hydrophobically modified polysaccharide;
for the temporary shaping and remodeling of keratin-containing fibers, in particular human hair, is particularly preferred.

A first essential constituent of cosmetic compositions used according to the invention is the hydrophobically modified (meth)acrylic acid copolymer a). The proportion by weight of the copolymer a) in the total weight of the cosmetic composition is preferably 0.05 to 5.0 wt. %, particularly preferably 0.1 to 4.0 wt. % and in particular 0.2 to 2.0 wt. %. Preferred copolymers a) have a thickening effect.

Copolymers which are derived from
   at least one monomer (A1) from the group of unsaturated carboxylic acids and unsaturated carboxylic acid esters, and
   at least one monomer (A2) from the group of unsaturated hydrophobically modified monomers are preferably used as hydrophobically modified (meth)acrylic acid copolymers a).

Preferred copolymers A are based on at least one monomer (A1) from the group of acrylic acid, methacrylic acid, $C_1$-$C_6$ alkyl acrylic acid esters, $C_1$-$C_6$ alkyl methacrylic acid esters. The acrylic acid esters and methacrylic acid esters are preferably esters of the individual acids with non-tertiary alkyl alcohols having alkyl residues of 1 to 12 carbon atoms, in particular 2 to 4 carbon atoms. Suitable monomers which can be mentioned are for example ethyl acrylate, ethyl methacrylate, propyl acrylate, propyl methacrylate, n-butyl acrylate, n-butyl methacrylate, isobutyl acrylate, 2-methylbutyl acrylate, 2-ethylhexyl acrylate, n-octyl acrylate, isooctyl acrylate, isooctyl methacrylate, isononyl acrylate and isodecyl acrylate.

The group of hydrophobically modified monomers (A2) refers to monomers having a hydrophobic substructure. Preferred monomers (A2) for their part are derived from the following two structural units:
- an unsaturated acid, preferably acrylic acid, methacrylic acid or itaconic acid;
- a $C_{8-40}$ alkyl chain, preferably a $C_{10-30}$ alkyl chain.

These two substructures can optionally be supplemented by a third structural unit from the group of polyoxyalkylene groups, preferably polyethylene glycol groups, polypropylene glycol groups or polyethylene glycol/polypropylene glycol groups.

$C_{10-30}$ alkyl acrylates, $C_{10-30}$ alkyl PEG acrylates, $C_{10-30}$ alkyl PEG methacrylates or $C_{10-30}$ alkyl PEG itaconates, for example, are used as the monomer (A2). Preferred monomers (A2) are selected from $C_{10-30}$ alkyl acrylates, $C_{10-30}$ alkyl PEG 20-25 acrylates, $C_{10-30}$ alkyl PEG 20-25 methacrylates or $C_{10-30}$ alkyl PEG 20-25 itaconates. Particularly preferred monomers (A2) are selected from the group of $C_{10-30}$ alkyl acrylates, steareth-20 methacrylates, beheneth-25 methacrylates, steareth-20 itaconates, ceteth-20 itaconates, palmeth-25 acrylates or $C_{10-30}$ alkyl PEG-20 itaconates.

In summary, copolymers a) are preferred which are formed from
- at least one monomer (A1) from the group of acrylic acid, methacrylic acid, $C_1$-$C_6$ alkyl acrylic acid esters, $C_1$-$C_6$ alkyl methacrylic acid esters,
- at least one monomer (A2) from the group of $C_{10-30}$ alkyl acrylates, $C_{10-30}$ alkyl PEG acrylates, $C_{10-30}$ alkyl PEG methacrylates or $C_{10-30}$ alkyl PEG itaconates.

Copolymers a) which are formed from
- at least one monomer (A1) from the group of acrylic acid, methacrylic acid, $C_1$-$C_6$ alkyl acrylic acid esters, $C_1$-$C_6$ alkyl methacrylic acid esters,
- at least one monomer (A2) from the group of $C_{10-30}$ alkyl acrylates, steareth-20 methacrylates, beheneth-25 methacrylates, steareth-20 itaconates, ceteth-20 itaconates, palmeth-25 acrylates or $C_{10-30}$ alkyl PEG-20 itaconates are particularly preferred.

Further preferred hydrophobically modified (meth)acrylic acid copolymers a) are formed from at least one monomer (A3) from the group of unsaturated amine-group-containing monomers in addition to the aforementioned monomers (A1) and (A2).

Monomers from the group of acrylamide, methacrylamide, mono-($C_1$-$C_4$) alkylamino ($C_1$-$C_4$) alkyl acrylate, di-($C_1$-$C_4$) alkylamino ($C_1$-$C_4$) alkyl acrylate, mono-($C_1$-$C_4$) alkylamino ($C_1$-$C_4$) alkyl methacrylate, di-($C_1$-$C_4$) alkylamino ($C_1$-$C_4$) alkyl methacrylate are preferably used as the monomer (A3).

Examples of preferred monomers (A2) are 2-(N,N-dimethylamino)ethyl acrylate, 2-(N,N-dimethylamino)ethyl methacrylates, 2-(N,N-diethylamino)ethyl acrylates, 2-(N,N-diethylamino)ethyl methacrylates, 3-(N,N-dimethylamino)propyl acrylate, 3-(N,N-dimethylamino)propyl methacrylate, 2-(N',N-dimethylamino)neopentyl acrylate, N'-(3-N,N-dimethylamino)propyl acrylamide, N'-(3-N,N-dimethylamino)propyl methacrylamide.

Copolymers A are preferred which are formed from
- at least one monomer (A1) from the group of acrylic acid, methacrylic acid, $C_1$-$C_6$ alkyl acrylic acid esters, $C_1$-$C_6$ alkyl methacrylic acid esters,
- at least one monomer (A2) from the group of $C_{10-30}$ alkyl PEG 20 itaconates,
- at least one monomer (A3) from the group of acrylamide, methacrylamide, mono-($C_1$-$C_4$) alkylamino ($C_1$-$C_4$) alkyl acrylate, di-($C_1$-$C_4$) alkylamino ($C_1$-$C_4$) alkyl acrylate, mono-($C_1$-$C_4$) alkylamino ($C_1$-$C_4$) alkyl methacrylate, di-($C_1$-$C_4$) alkylamino ($C_1$-$C_4$) alkyl methacrylate.

Copolymers a) which are particularly preferably used are crosslinked. Crosslinking improves the tactile properties of the agents used according to the invention. In addition, the hair-fixing effect of these agents, in particular when used in small amounts, is improved.

In summary, cosmetic compositions which are preferably used according to the invention are characterized in that the copolymer a) is selected from the group of compounds having the INCI names Acrylates/$C_{10-30}$ Alkyl Acrylate Crosspolymer, Acrylates/Steareth-20 Methacrylate Crosspolymer, Acrylates/Steareth-20 Methacrylate Copolymer, Acrylates/Beheneth-25 Methacrylate Copolymer, Acrylates/Steareth-20 Itaconate Copolymer, Acrylates/Ceteth-20 Itaconate Copolymer, Acrylates/Palmeth-25 Acrylate Copolymer, Acrylates/Aminoacrylates/$C_{10-30}$ Alkyl PEG-20 Itaconate Copolymer Corresponding polymers are available for example under the trade names Ultrez® 21, Pemulen® TR1, Aculyn® 22, Aculyn® 28, Aculyn® 88, Structure® 2001, Structure® 3001, Synthalen® W2000 and Structure® Plus. The copolymer a) is particularly preferably selected from the group of compounds having the INCI name Acrylates/$C_{10-30}$ Alkyl Acrylate Crosspolymer.

As the second essential constituent the cosmetic compositions used according to the invention contain at least one hydrophobically modified polysaccharide b). The proportion by weight of the polysaccharide b) in the total weight of the cosmetic composition is preferably 0.1 to 8.0 wt. %, particularly preferably 0.5 to 6.0 wt. % and in particular 1.0 to 4.0 wt. %. Preferred polysaccharides b) do not have a thickening effect.

Preferred hydrophobically modified polysaccharides have saturated or unsaturated alkyl residues and/or saturated or unsaturated arylalkyl residues with six to thirty carbon atoms. Particularly preferred hydrophobically modified polysaccharides are characterized by saturated or unsaturated $C_{6-30}$ alkyl residues, preferably by saturated or unsaturated $C_{8-18}$ alkyl residues, in particular by unsaturated $C_{8-18}$ alkyl residues. Corresponding hydrophobically modified polysaccharides are obtainable for example by etherification or esterification of the hydroxyl groups of polysaccharides. Starch ethers or starch esters are formed in this way, for example.

In a first preferred embodiment the polysaccharide b) is selected from the group of starch ethers. Starch ethers by way of example are obtained by the etherification of starch with tetramethylol acetylenediurea.

It is particularly preferable, however, for the polysaccharide b) to be selected from the group of starch esters. The group of starch esters comprises in particular also the sodium and/or aluminum salts of low-substituted semi-esters of starch, for example sodium starch octenylsuccinates or aluminum starch octenylsuccinates, which are obtainable for example by reacting starch with octenylsuccinic anhydride. Cosmetic compositions which are particularly preferably used are characterized in that the polysaccharide b) is selected from the group of starch octenylsuccinates, in particular from the compounds having the INCI name Sodium Starch Octenylsuccinate, but preferably from the group having the INCI name Aluminum Starch Octenylsuccinate.

The starch esters have proved to be superior to the starch ethers in terms of their cosmetic and tactile properties.

For the use according to the invention it has proved advantageous to maintain certain weight ratios between the copolymer a) and the polysaccharide b). It is therefore preferable according to the invention for the weight ratio of the copolymer a) to the polysaccharide b) to be 2:1 to 1:30, preferably 1:1 to 1:20 and in particular 1:2 to 1:10.

In addition to the copolymers a) and polysaccharides b) described above, the cosmetic compositions used according to the invention can contain further active agents, auxiliary substances and care substances.

A first group of active agents that are preferably used are waxes. Preferred waxes have a melting point in the range from 40° C. to 90° C., particularly preferably in the range from 50° C. to 85° C. and in particular in the range from 50° C. to 75° C. The proportion by weight of waxes relative to the total weight of the cosmetic preparation is preferably 0.1 to 10 wt. %, particularly preferably 0.2 to 8.0 wt. % and in particular 0.5 to 5.0 wt. %.

In principle, all waxes which melt in the cited temperature range and are physiologically acceptable can be used. Particularly preferred waxes according to the invention are beeswax (cera alba), carnauba wax, candelilla wax, montan wax, microcrystalline waxes (microcrystalline paraffins) and cetyl palmitate.

The teaching according to the invention also encompasses the combined use of several waxes. Thus an addition of small amounts of carnauba wax can be used to increase the melting and dropping point of another wax and to reduce its stickiness. In addition, a range of wax blends, optionally mixed with further additives, is commercially available.

Examples of blends which are preferably used according to the invention are those available under the names "Spezialwachs 7686 OE" (a blend of cetyl palmitate, beeswax, microcrystalline wax and polyethylene, with a melting range from 73-75° C.; manufacturer: Kahl & Co), Polywax® GP 200 (a blend of stearyl alcohol and polyethylene glycol stearate with a melting point of 47-51° C.; manufacturer: Croda) and "Weichceresin® FL 400" (a vaseline/vaseline oil/wax blend with a melting point of 50-54° C.; manufacturer: Parafluid Mineralölgesellschaft).

In a special embodiment of the invention "liquid waxes", such as jojoba oil for example, can also be used in addition to the compounds which are conventionally defined as waxes.

In summary, cosmetic compositions are preferably used in particular which, relative to their total weight, contain 0.1 to 10 wt. %, preferably 0.2 to 8.0 wt. % and in particular 0.5 to 5.0 wt. % of at least one wax, preferably at least one wax from the group of beeswax and carnauba wax. The addition of wax to the cosmetic preparations used according to the invention was able to bring about an unexpected increase in volume of the temporarily shaped keratinic fibers.

The present application also provides a cosmetic composition, containing
a) at least one hydrophobically modified (meth)acrylic acid copolymer;
b) at least one hydrophobically modified polysaccharide;
c) at least one wax.

The preferred features of cosmetic compositions according to the invention correspond with the necessary changes to the preferred features of the agents used in the context of the use according to the invention.

The group of film-forming polymers forms a further preferred constituent of cosmetic compositions used according to the invention. These film-forming polymers are not identical to the hydrophobically modified (meth)acrylic acid copolymer a) described above. The proportion by weight of the film-forming polymer in the total weight of the cosmetic composition is by preference 0.1 to 8.0 wt. %, preferably 0.5 to 6.0 wt. % and in particular 1.0 to 4.0 wt. %.

Non-ionic polymers are particularly preferably used as film-forming polymers. Suitable non-ionic polymers are for example:

vinylpyrrolidone/vinyl ester copolymers, such as are sold for example under the trademark Luviskol® (BASF). Luviskol® VA 64 and Luviskol® VA 73, both of which are vinylpyrrolidone/vinyl acetate copolymers, are preferred non-ionic polymers.

cellulose ethers, such as hydroxypropyl cellulose, hydroxyethyl cellulose and methylhydroxypropyl cellulose, such as are sold for example under the trademarks Culminal® and Benecel® (AQUALON).

shellac.

polyvinylpyrrolidones, such as are sold for example under the name Luviskol®(BASF).

siloxanes. These siloxanes can be both water-soluble and water-insoluble. Both volatile and non-volatile siloxanes are suitable, wherein compounds whose boiling point under normal pressure is above 200° C. are understood to be non-volatile siloxanes. Preferred siloxanes are polydialkyl siloxanes, such as for example polydimethyl siloxane, polyalkylaryl siloxanes, such as for example polyphenylmethyl siloxane, ethoxylated polydialkyl siloxanes as well as polydialkyl siloxanes containing amine and/or hydroxyl groups.

glycoside-substituted silicones.

Polyvinylpyrrolidones (INCI name: PVP) are preferred in particular according to the invention.

Protein hydrolysates and/or derivatives thereof can be used as the care substance. Protein hydrolysates are mixtures of products which are obtained by acidically, basically or enzymatically catalyzed breakdown of proteins. According to the invention the term protein hydrolysates is also understood to include total hydrolysates and individual amino acids and derivatives thereof as well as mixtures of different amino acids. The molecular weight of the protein hydrolysates for use according to the invention is between 75, the molecular weight for glycine, and 200,000; the molecular weight is preferably 75 to 50,000 and particularly preferably 75 to 20,000 daltons.

A further group of care substances are the vitamins, provitamins, vitamin precursors and/or derivatives thereof. Those vitamins, provitamins and vitamin precursors that are conventionally assigned to groups A, B, C, E, F and H are preferred according to the invention.

Further care substances are glycerol, propylene glycol, panthenol and sorbitol.

Plant extracts and also mono- or oligosaccharides and/or lipids can be used as the care substance.

Oil bodies form a further group of care substances. The natural and synthetic cosmetic oil bodies include for example vegetable oils, liquid paraffin oils, isoparaffin oils and synthetic hydrocarbons along with di-n-alkyl ethers having in total between 12 and 36 C atoms, in particular 12 to 24 C atoms. Oil bodies from the group of silicone oils are moreover preferred. The group of silicone oils includes in particular dimethicones, which also include cyclomethicones, amino-functional silicones and dimethiconols. The dimethicones can be both linear and branched and also cyclic or cyclic and branched. Suitable silicone oils or silicone gums are in particular dialkyl and alkylaryl siloxanes, such as for example dimethyl polysiloxane and methyl phenyl polysiloxane, and the alkoxylated, quaternized or also anionic derivatives thereof. Cyclic and linear polydialkyl siloxanes, the alkoxylated and/or aminated derivatives thereof, dihydroxypolydimethyl siloxanes and polyphenyl alkyl siloxanes are preferred.

Ester oils, in other words esters of $C_6$-$C_{30}$ fatty acids with $C_2$-$C_{30}$ fatty alcohols, preferably monoesters of fatty acids with alcohols having 2 to 24 C atoms, such as for example isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V), are further preferred caring oil bodies.

Furthermore, dicarboxylic acid esters, symmetrical, asymmetrical or cyclic esters of carbonic acid with fatty alcohols, tri-fatty acid esters of saturated and/or unsaturated linear and/or branched fatty acids with glycerol or fatty acid partial glycerides, which are understood to be monoglycerides, diglycerides and technical mixtures thereof, are suitable as care substances.

The water content of cosmetic compositions that are preferably used is 30 to 80 wt. %, preferably 40 to 70 wt. % and in particular 45 to 65 wt. %.

The composition of a number of cosmetic agents that are used can be taken from the tables below (amounts in wt. % relative to the total weight of the cosmetic agent unless otherwise specified).

|  | Formula 1 | Formula 2 | Formula 3 | Formula 4 | Formula 5 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

|  | Formula 6 | Formula 7 | Formula 8 | Formula 9 | Formula 10 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Water | 30 to 80 | 40 to 70 | 45 to 65 | 62 | 33 |
| Misc | to 100 | to 100 | to 100 | to 100 | to 100 |

|  | Formula 11 | Formula 12 | Formula 13 | Formula 14 | Formula 15 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

|  | Formula 16 | Formula 17 | Formula 18 | Formula 19 | Formula 20 |
|---|---|---|---|---|---|
| Acrylates/Steareth-20 Methacrylate Crosspolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

|  | Formula 21 | Formula 22 | Formula 23 | Formula 24 | Formula 25 |
|---|---|---|---|---|---|
| Acrylates/Steareth-20 Methacrylate Copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

-continued

|  | Formula 26 | Formula 27 | Formula 28 | Formula 29 | Formula 30 |
|---|---|---|---|---|---|
| Acrylates/Beheneth-25 Methacrylate Copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

|  | Formula 31 | Formula 32 | Formula 33 | Formula 34 | Formula 35 |
|---|---|---|---|---|---|
| Acrylates/Steareth-20 Itaconate Copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

|  | Formula 36 | Formula 37 | Formula 38 | Formula 39 | Formula 40 |
|---|---|---|---|---|---|
| Acrylates/Ceteth-20 Itaconate Copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

|  | Formula 41 | Formula 42 | Formula 43 | Formula 44 | Formula 45 |
|---|---|---|---|---|---|
| Acrylates/Palmeth-25 Acrylate Copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

|  | Formula 46 | Formula 47 | Formula 48 | Formula 49 | Formula 50 |
|---|---|---|---|---|---|
| Acrylates/Aminoacrylates/ $C_{10-30}$ Alkyl PEG-20 Itaconate Copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Misc | to 100 | to 100 | to 100 | to 100 | to 100 |

|  | Formula 51 | Formula 52 | Formula 53 | Formula 54 | Formula 55 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Misc | to 100 | to 100 | to 100 | to 100 | to 100 |

|  | Formula 56 | Formula 57 | Formula 58 | Formula 59 | Formula 60 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Water |  | 30 to 80 | 40 to 70 | 45 to 65 | 62 | 33 |
| Misc | to 100 | to 100 | to 100 | to 100 | to 100 |

-continued

|  | Formula 61 | Formula 62 | Formula 63 | Formula 64 | Formula 65 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Misc | to 100 | to 100 | to 100 | to 100 | to 100 |

|  | Formula 66 | Formula 67 | Formula 68 | Formula 69 | Formula 70 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Misc | to 100 | to 100 | to 100 | to 100 | to 100 |

|  | Formula 71 | Formula 72 | Formula 73 | Formula 74 | Formula 75 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Misc | to 100 | to 100 | to 100 | to 100 | to 100 |

|  | Formula 76 | Formula 77 | Formula 78 | Formula 79 | Formula 80 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Beeswax | 0.1 to 10 | 0.2 to 8.0 | 0.5 to 5.0 | 3.0 | 8.7 |
| Misc | to 100 | to 100 | to 100 | to 100 | to 100 |

|  | Formula 81 | Formula 82 | Formula 83 | Formula 84 | Formula 85 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Beeswax | 0.1 to 10 | 0.2 to 8.0 | 0.5 to 5.0 | 3.0 | 8.7 |
| Misc | to 100 | to 100 | to 100 | to 100 | to 100 |

|  | Formula 86 | Formula 87 | Formula 88 | Formula 89 | Formula 90 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Beeswax | 0.1 to 10 | 0.2 to 8.0 | 0.5 to 5.0 | 3.0 | 8.7 |
| Misc | to 100 | to 100 | to 100 | to 100 | to 100 |

|  | Formula 91 | Formula 92 | Formula 93 | Formula 94 | Formula 95 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |

-continued

| | | | | | |
|---|---|---|---|---|---|
| Film-forming polymer* | 0.1 to 8.0 | 0.5 to 6.0 | 1.0 to 4.0 | 1.2 | 3.8 |
| Misc | to 100 | to 100 | to 100 | to 100 | to 100 |

| | Formula 96 | Formula 97 | Formula 98 | Formula 99 | Formula 100 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Film-forming polymer* | 0.1 to 8.0 | 0.5 to 6.0 | 1.0 to 4.0 | 1.2 | 3.8 |
| Misc | to 100 | to 100 | to 100 | to 100 | to 100 |

| | Formula 101 | Formula 102 | Formula 103 | Formula 104 | Formula 105 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Film-forming polymer* | 0.1 to 8.0 | 0.5 to 6.0 | 1.0 to 4.0 | 1.2 | 3.8 |
| Misc | to 100 | to 100 | to 100 | to 100 | to 100 |

| | Formula 106 | Formula 107 | Formula 108 | Formula 109 | Formula 110 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Polyvinylpyrrolidone | 0.1 to 8.0 | 0.5 to 6.0 | 1.0 to 4.0 | 1.2 | 3.8 |
| Misc | to 100 | to 100 | to 100 | to 100 | to 100 |

| | Formula 111 | Formula 112 | Formula 113 | Formula 114 | Formula 115 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Polyvinylpyrrolidone | 0.1 to 8.0 | 0.5 to 6.0 | 1.0 to 4.0 | 1.2 | 3.8 |
| Misc | to 100 | to 100 | to 100 | to 100 | to 100 |

| | Formula 116 | Formula 117 | Formula 118 | Formula 119 | Formula 120 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Polyvinylpyrrolidone | 0.1 to 8.0 | 0.5 to 6.0 | 1.0 to 4.0 | 1.2 | 3.8 |
| Misc | to 100 | to 100 | to 100 | to 100 | to 100 |

| | Formula 121 | Formula 122 | Formula 123 | Formula 124 | Formula 125 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Water | 30 to 80 | 40 to 70 | 45 to 65 | 62 | 33 |
| Misc | to 100 | to 100 | to 100 | to 100 | to 100 |

| | Formula 126 | Formula 127 | Formula 128 | Formula 129 | Formula 130 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |

|  | | | | | |
|---|---|---|---|---|---|
| Hydrophobically modified polysaccharide | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Water | 30 to 80 | 40 to 70 | 45 to 65 | 62 | 33 |
| Misc | to 100 | to 100 | to 100 | to 100 | to 100 |

|  | Formula 131 | Formula 132 | Formula 133 | Formula 134 | Formula 135 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Water | 30 to 80 | 40 to 70 | 45 to 65 | 62 | 33 |
| Misc | to 100 | to 100 | to 100 | to 100 | to 100 |

|  | Formula 136 | Formula 137 | Formula 138 | Formula 139 | Formula 140 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Beeswax | 0.1 to 10 | 0.2 to 8.0 | 0.5 to 5.0 | 3.0 | 8.7 |
| Water | 30 to 80 | 40 to 70 | 45 to 65 | 62 | 33 |
| Misc | to 100 | to 100 | to 100 | to 100 | to 100 |

|  | Formula 141 | Formula 142 | Formula 143 | Formula 144 | Formula 145 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Film-forming polymer* | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

|  | Formula 146 | Formula 147 | Formula 148 | Formula 149 | Formula 150 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Film-forming polymer* | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

|  | Formula 151 | Formula 152 | Formula 153 | Formula 154 | Formula 155 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Film-forming polymer* | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

|  | Formula 156 | Formula 157 | Formula 158 | Formula 159 | Formula 160 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Polyvinylpyrrolidone | 0.1 to 8.0 | 0.5 to 6.0 | 1.0 to 4.0 | 1.2 | 3.8 |

-continued

| | | | | | |
|---|---|---|---|---|---|
| Water | 30 to 80 | 40 to 70 | 45 to 65 | 62 | 33 |
| Misc | to 100 | to 100 | to 100 | to 100 | to 100 |

| | Formula 161 | Formula 162 | Formula 163 | Formula 164 | Formula 165 |
|---|---|---|---|---|---|
| Hydrophobically modified (meth)acrylic acid copolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Film-forming polymer* | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

| | Formula 161 | Formula 162 | Formula 163 | Formula 164 | Formula 165 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Hydrophobically modified polysaccharide | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Film-forming polymer* | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

| | Formula 166 | Formula 167 | Formula 168 | Formula 169 | Formula 170 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Film-forming polymer* | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

| | Formula 171 | Formula 172 | Formula 173 | Formula 174 | Formula 175 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Beeswax | 0.1 to 10 | 0.2 to 8.0 | 0.5 to 5.0 | 3.0 | 8.7 |
| Film-forming polymer* | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

| | Formula 176 | Formula 177 | Formula 178 | Formula 179 | Formula 180 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Wax | 0.1 to 10 | 0.2 to 8.0 | 0.5 to 5.0 | 3.0 | 8.7 |
| Polyvinylpyrrolidone | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

| | Formula 181 | Formula 182 | Formula 183 | Formula 184 | Formula 185 |
|---|---|---|---|---|---|
| Acrylates/C10-30 Alkyl Acrylate Crosspolymer | 0.05 to 5.0 | 0.1 to 4.0 | 0.2 to 2.0 | 0.6 | 0.3 |
| Aluminum Starch Octenylsuccinate | 0.1 to 8.0 | 0.5 to 6.0 | 1.0 to 4.0 | 2.7 | 1.2 |
| Beeswax | 0.1 to 10 | 0.2 to 8.0 | 0.5 to 5.0 | 3.0 | 8.7 |

-continued

| | | | | | |
|---|---|---|---|---|---|
| Polyvinylpyrrolidone | 0.1 to 8.0 | 0.5 to 6.0 | 1.0 to 4.0 | 1.2 | 3.8 |
| Water | 30 to 80 | 40 to 70 | 45 to 65 | 62 | 33 |
| Misc | to 100 | to 100 | to 100 | to 100 | to 100 |

*not a hydrophobically modified (meth)acrylic acid copolymer

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for temporary shaping of keratin-containing fibers, comprising:
    applying to the keratin-containing fibers a cosmetic composition comprising
    a) at least one hydrophobically modified (meth)acrylic acid copolymer;
    b) at least one hydrophobically modified polysaccharide; and
    c) at least one wax;
    wherein at least one wax is selected from the group consisting of beeswax and carnauba wax;
    wherein the wax is present in an amount 0.1 wt % to 10 wt % based on the total weight of the cosmetic composition; and
    wherein the hydrophobically modified (meth)acrylic copolymer is present in an amount of 0.05 wt % to 5.0 wt % based on the total weight of the cosmetic composition.

2. The method of claim 1, wherein the hydrophobically modified (meth)acrylic acid copolymer is crosslinked.

3. The method of claim 1, wherein the hydrophobically modified (meth)acrylic acid copolymer is a compound having the INCI name acrylates/C10-30 alkyl acrylate crosspolymer.

4. The method of claim 1, wherein the hydrophobically modified (meth)acrylic copolymer is present in an amount of 0.1 wt % to 4.0 wt % based on the total weight of the cosmetic composition.

5. The method of claim 1, wherein the hydrophobically modified (meth)acrylic copolymer is present in an amount of 0.2 wt % to 2.0 wt % based on the total weight of the cosmetic composition.

6. The method of claim 1, wherein the at least one hydrophobically modified polysaccharide includes a starch ester.

7. The method of claim 1, wherein the hydrophobically modified polysaccharide is a starch octenylsuccinates.

8. The method of claim 7, wherein the starch octenylsuccinate is aluminum starch octenylsuccinate.

9. The method of claim 1, wherein the hydrophobically modified polysaccharide is present in an amount of 0.1 wt % to 8.0 wt % based on the total weight of the cosmetic composition.

10. The method of claim 1, wherein the hydrophobically modified polysaccharide is present in an amount of 0.5 wt % to 6.0 wt % based on the total weight of the cosmetic composition.

11. The method of claim 1, wherein the hydrophobically modified polysaccharide is present in an amount of 1.0 wt % to 4.0 wt % based on the total weight of the cosmetic composition.

12. The method according to claim 1, wherein the wax is present in an amount 0.2 wt % to 8.0 wt % based on the total weight of the cosmetic composition.

13. The method according to claim 1, wherein the cosmetic composition further comprises, based on the total weight of the cosmetic composition, 0.1 wt % to 8.0 wt % of at least one film-forming polymer that is different from the hydrophobically modified (meth)acrylic acid copolymer.

14. The method according to claim 13, wherein the at least one film-forming polymer that is different from the hydrophobically modified (meth)acrylic acid copolymer is a polyvinylpyrrolidone.

15. The method according to claim 13, wherein the at least one film-forming polymer that is different from the hydrophobically modified (meth)acrylic acid copolymer is present in an amount 0.5 to 6.0 wt % based on the total weight of the cosmetic composition.

* * * * *